United States Patent [19]
Gianos et al.

[11] 4,014,653
[45] Mar. 29, 1977

[54] MICRO-FILTER

[75] Inventors: Edward A. Gianos, Cos Cob, Conn.;
H. Eric Hunter, Westwood, Calif.;
Edgar A. Lazo-Wasem, New Canaan, Conn.

[73] Assignee: Denver Chemical Manufacturing Company, Stamford, Conn.

[22] Filed: Dec. 26, 1974

[21] Appl. No.: 536,632

[52] U.S. Cl. .............................. 23/259; 23/292; 128/2 F; 210/455; 210/482

[51] Int. Cl.² ....................................... G01F 15/12

[58] Field of Search ............ 23/259, 292; 210/455, 210/482; 128/2 F

[56] References Cited

UNITED STATES PATENTS

| | | | |
|---|---|---|---|
| 865,691 | 9/1907 | Fox | 210/446 X |
| 938,279 | 10/1909 | Schultze | 23/259 |
| 2,341,414 | 2/1944 | Polivka | 210/446 X |
| 3,215,500 | 11/1965 | Bittner | 23/259 |
| 3,322,114 | 5/1967 | Portnoy et al. | 23/230 B |
| 3,682,315 | 8/1972 | Haller | 210/477 X |
| 3,805,998 | 4/1974 | Croslin | 23/259 X |
| 3,874,851 | 4/1975 | Wilkins et al. | 23/259 X |

*Primary Examiner*—R.E. Serwin
*Assistant Examiner*—Arnold Turk
*Attorney, Agent, or Firm*—Gordon W. Hueschen

[57] ABSTRACT

Microliter sized samples of filtered urine or the like are obtained by taking up a few drops of urine into a bulb-type micro-syringe inserting the nozzle thereof tightly into the inlet passageway of a micro-filter having a disc of filter paper as the filtering medium held firmly between the inlet passageway and an outlet passageway and squeezing the bulb of the micro-syringe to force the urine through the filter paper. The outlet passageway is constricted in size and shape to discharge the filtered urine in drops. The filtered urine then comes through in uniform drops of predetermined size which are utilized in a testing procedure, for example, in a direct agglutination test for pregnancy.

5 Claims, 4 Drawing Figures

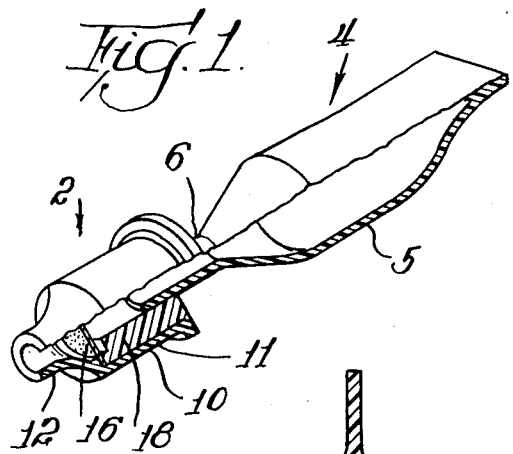
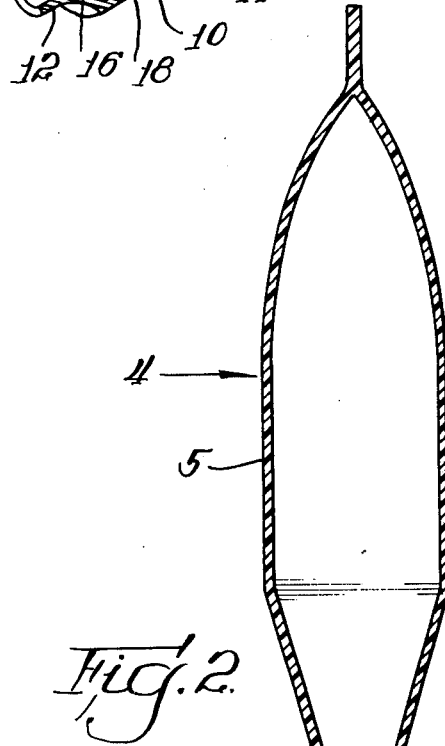
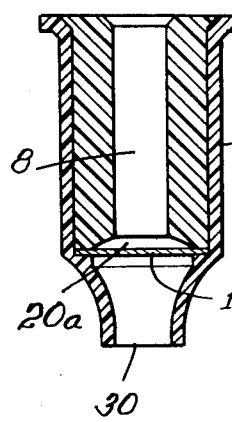
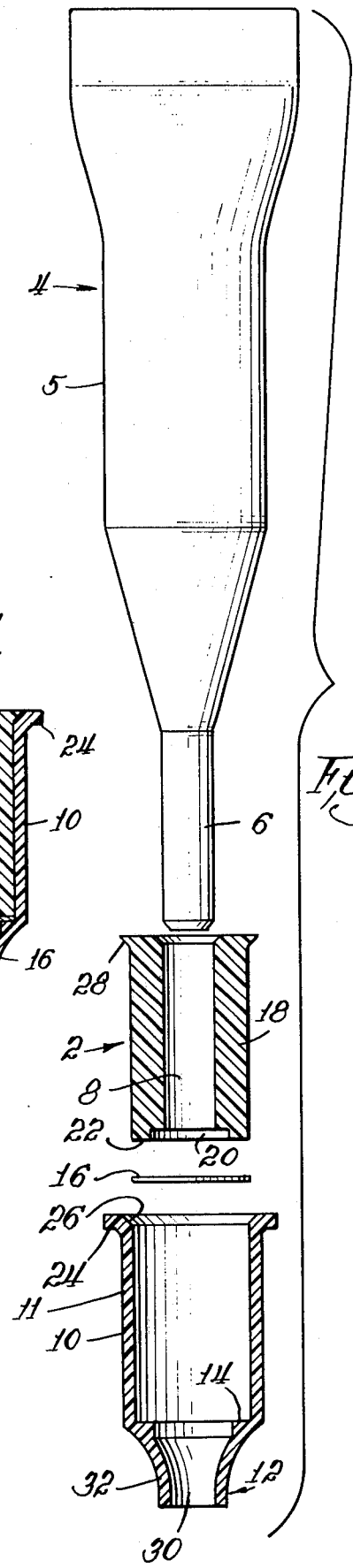
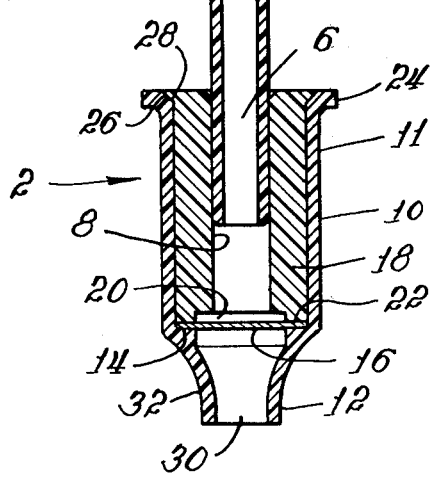

MICRO-FILTER

BACKGROUND OF INVENTION

1. Field of Invention

The invention relates to a method and apparatus for obtaining and preparing samples of biological liquid, for example, urine, for testing, for example, direct agglutination pregnancy testing.

2. Prior Art

Many diagnostic tests on urine require prior filtration. For example, pregnancy tests. Usually filtration is accomplished by use of filter paper, funnel and a collection vessel. An improvement on this is a plastic tube with filter fibers such as cotton placed at one end of the tube. With a plastic pipette the liquid is delivered into the filtering tube by squeezing, for forced passage through the filter fibers. This device has the disadvantage that the efficiency of filtration will depend upon the degree of packing of the filter fibers whereby too densely packed a filter may remove too much of the material in the urine whereas too loosely packed a filter may not filter sufficiently the interfering suspended solids.

OBJECTS

It is an object of the invention to provide a new and improved method and apparatus for filtering microliter samples of biological liquid in preparing them for testing. It is a further object of the invention to avoid the disadvantages of the prior art and to obtain such other advantages as will appear as the description proceeds.

SUMMARY OF THE INVENTION

The objects of the invention are accomplished in a method and apparatus in which a few drops of the biological liquid to be tested is taken up in a bulb-type micro-syringe (mini-plastic pipette), the nozzle tightly inserted into the inlet passageway of a micro-filter having a disc of filter paper held firmly between the inlet passageway and an outlet passageway, the bulb of the micro-syringe is squeezed to force liquid through the filter disc, and the filter effluent is constrained by the size and shape of the outlet passageway to cause it to be discharged one drop at a time in uniformly sized drops.

BRIEF DESCRIPTION OF THE DRAWINGS

FIG. 1 is an isometric view in partial cross-section.
FIG. 2 is a longitudinal cross-section.
FIG. 3 is an exploded cross-section.
FIG. 4 is a longitudinal cross-section of a modified form of the filter portion.

DESCRIPTION OF THE PREFERRED EMBODIMENTS

Referring now particularly to the drawings, there is illustrated a device having a filter portion 2 and a bulb-type portion 4. The filter portion advantageously is made up of a rigid plastic such as polypropylene, polystyrene, nylon, or the like, whereas the bulb-type syringe portion 4 is made up of pliable plastic, e.g., polyethylene or like deformable plastic having good recovery properties. The bulb-type syringe portion 4 has a nozzle 6 adapted to fit into the inlet passageway 8 of the filter portion 2. The size of the inlet passageway and the nozzle 6 are complementary to provide a tight friction fit so that when the bulb portion 5 is squeezed the pressure is transferred to the passageway 8.

The filter portion 2 is made up of a cylindrical outer shell 10 having a cylindrical upper part 11 and a constricted bottom portion 12. At the bottom of the cylindrical bottom portion 11 is an annular shoulder 14 on which rests a disc of filter paper 16. The filter paper is held tightly pressed against the annular shoulder 14 by a cylindrical plug 18 having the axially located passageway 8 previously alluded to. The outside diameter of plug 18 is the same as the inside diameter of the cylindrical upper portion 11 of the shell 10 so as to provide a tight friction fit. The inlet passageway 8 has an enlarged bottom portion 20 extending over the major area of the bottom face of the plug 18 thereby leaving an annular portion 22 adapted to firmly press the filter paper disc 16 against the annular shoulder 14.

As shown more particularly in FIG. 3 the shell 10 has a rim 24 around the opening thereof having an outward bevel at 26. The plug 18 has a corresponding outwardly beveled flange 26 which is complementary to the bevel 26 of the flange 24. This provides a limit for the inward thrust of the plug 18 and a telltale to show when the plug is not properly seated against the filter disc 16. The inside diameters of the annular portion 22 and the annular shoulder 14 are the same and the enlarged portion 20 has an area coextensive with the area of the filter disc 16 which is not clamped between the annular shoulder 14 and the annular base portion 22 in order to obtain maximum utilization of the filter capacity.

As shown in FIG. 3, the enlarged portion 20 is cylindrical in shape whereas in FIG. 4 the enlarged portion 20a is shaped as a segment of a sphere. In other words, it is concave in shape. The volume of the enlarged portion 20 or 20a and the rest of the inlet passageway 8 is small compared with the volume of the bulb 5 and the nozzle 6 so that an adequate head of liquid can always be maintained on the filter disc 16.

The constricted portion 12 has an orifice 30 and sides 32 tapering from the shell 10 to the orifice 30. Advantageously, the sides 32 bulge inwardly so as further to reduce the volume of the constricted portion 12.

In order to accomplish one of the prime purposes of the invention, namely, the ability to deliver a single drop quantity of the liquid of a precise volume, the constricted portion 12 should have a volume less than that of a drop of a liquid to be tested. Thus in general, it should have a volume less than about 50 micro-liters and the orifice 30 should have a diameter not greater than about one-half of the diameter of the drop of the liquid being tested, in general not greater than about 2 millimeters. Thus, by limiting the liquid holdup between the filter paper 16 and the orifice 30 to less than the volume of a single drop of the liquid to be tested and keeping the orifice small with reference to the drop size, single drops will be delivered from the orifice as the liquid to be filtered is forced through the filter disc 16.

Thus, in one use of the invention the bulb-type syringe 4 is dipped into a sample of urine, a few drops of urine sucked into it, the nozzle then inserted into the inlet passageway of the micro-filter, the bulb squeezed, forcing the urine through the filter as needed to cause one drop of the filtered urine to drop onto a microscope slide. The sample of urine thus deposited on the slide is examined according to procedures already well known in the art to determine whether or not pregnancy is indicated.

It is to be understood that the invention is not to be limited to the exact details of operation or structure shown and described as obvious modifications and equipment will be apparent to one skilled in the art.

We claim:

1. In a micro-filter for filtering microliter quantities of liquid which comprises a flow passageway having inlet and outlet portions and a middle portion, said outlet portion including an orifice, means for holding filter material in the middle portion of said passageway, a bulb-type collapsible micro-syringe with a single terminal nozzle opening through which liquid is drawn into the bulb portion thereof and discharged therefrom, said inlet portion of said passageway and the nozzle being complementarily shaped so that the nozzle can be inserted into the inlet portion of the passageway in liquid tight engagement, whereby liquid from said micro-syringe can be forced into the passageway by finger pressure and the pressure maintained until the desired amount of liquid has passed through the filter material, the improvement wherein the middle portion has a larger cross-section than the inlet, the outlet portion tapers from said middle portion to said orifice, and wherein the outlet portion of the passageway has a volume not greater than about fifty microliters and the diameter at the orifice thereof is not greater than about two millimeters.

2. The micro-filter of claim 1, in which the flow passageway having said inlet, outlet and middle portions comprises a shell having a cylindrical upper portion, a bottom portion tapering to said orifice, an annular shoulder at the juncture of the upper and bottom portions, a disc of filter paper resting on said shoulder, a cylindrical plug complementary to the cylindrical portion of said shell and adapted to be inserted thereinto in friction tight engagement and to engage the filter paper against said shoulder, said plug having an axial bore which at the inlet portion of said passageway has a diameter complementary to the outside diameter of the nozzle of the bulb-type syringe and at the portion opposite the filter disc has a larger diameter and substantially the same diameter at the filter as that of the annular shoulder.

3. The micro-filter of claim 1 in which the bulb-type syringe is made of pliable plastic and the micro-filter is of rigid plastic.

4. The micro-filter of claim 3 in which the bulb-type syringe is made of polyethylene.

5. The method of obtaining and preparing samples for testing which comprises taking up a few drops of a liquid to be tested in a bulb-type micro-syringe, inserting the nozzle of the micro-syringe tightly into an inlet passageway of a micro-filter having a disc of filter paper held firmly between the inlet passageway and an outlet passageway, squeezing the bulb of the micro-syringe to force liquid through the filter paper but first allowing it to expand over a relatively large surface area of filter paper to minimize resistance to flow of liquid through the filter paper, and thereafter constraining the filter effluent to cause it to be discharged in uniformly sized drops, in which method the filter effluent is constrained to a volume of less than about fifty microliters, being the volume of less than one drop of liquid being tested.

* * * * *